(12) United States Patent
Murray (10) Patent No.: US 8,905,987 B2
(45) Date of Patent: Dec. 9, 2014

(54) DRAINABLE OSTOMY POUCH WITH CONCEALED DRAIN CHUTE

(75) Inventor: Kimberly Murray, Pittsburgh, PA (US)

(73) Assignee: Convatec Technologies Inc., Las Vegas, NV (US)

(*) Notice: Subject to any disclaimer, the term of this patent is extended or adjusted under 35 U.S.C. 154(b) by 0 days.

(21) Appl. No.: 12/936,258

(22) PCT Filed: Apr. 7, 2009

(86) PCT No.: PCT/US2009/039764
§ 371 (c)(1),
(2), (4) Date: Oct. 4, 2010

(87) PCT Pub. No.: WO2009/124324
PCT Pub. Date: Oct. 8, 2009

(65) Prior Publication Data
US 2011/0028924 A1   Feb. 3, 2011

Related U.S. Application Data

(60) Provisional application No. 61/042,427, filed on Apr. 4, 2008.

(51) Int. Cl.
*A61F 5/44*   (2006.01)
*B65D 33/24*   (2006.01)
*A61F 5/445*   (2006.01)

(52) U.S. Cl.
CPC ............. *A61F 5/4407* (2013.01); *A61F 5/445* (2013.01)
USPC ........... 604/332; 604/334; 604/337; 604/339; 383/57; 383/84

(58) Field of Classification Search
USPC ................ 604/183–186, 257–263, 317–357, 604/540–544; 383/50, 57, 61.1–61.5, 67, 383/81–99; 4/144.1
See application file for complete search history.

(56) References Cited

U.S. PATENT DOCUMENTS

| | | | |
|---|---|---|---|
| 2,520,831 A | 8/1950 | Chincholl | |
| 3,507,282 A | 4/1970 | Burding | |
| 3,825,005 A | 7/1974 | Fenton | |
| 4,519,797 A | 5/1985 | Hall | |
| 4,676,851 A | 6/1987 | Scheibner | |
| 5,248,308 A | 9/1993 | Von Emster | |
| 5,676,466 A | 10/1997 | Lindenbeck | |
| 5,968,023 A * | 10/1999 | Olsen | ............... 604/334 |
| 6,589,221 B1 | 7/2003 | Andersen | |
| 6,780,172 B2 | 8/2004 | Olsen et al. | |
| 7,306,581 B2 | 12/2007 | Breakwell | |

(Continued)

OTHER PUBLICATIONS

"Seam." Webster's Seventh New Collegiate Dictionary. G. & C. Merriam Co. 1967. p. 777.*

*Primary Examiner* — Loan H Thanh
*Assistant Examiner* — Joshua Lee
(74) *Attorney, Agent, or Firm* — Lorelei P. Westin, Esq.

(57) ABSTRACT

A drainable ostomy pouch includes a collection portion and a drain chute portion extending from the collection portion and having a discharge opening for permitting emptying of contents from the pouch. The drain chute is foldable between an open condition in which the drain chute portion is extended from the collection portion, and a closed condition in which the drain chute portion is folded towards the collection portion. At least one flap retains the folded drain chute portion.

11 Claims, 10 Drawing Sheets

(56) References Cited

U.S. PATENT DOCUMENTS

| | | | |
|---|---|---|---|
| 7,842,018 B2* | 11/2010 | Schena et al. | 604/344 |
| 7,879,016 B2* | 2/2011 | Mandzij et al. | 604/335 |
| 7,947,025 B2* | 5/2011 | Buglino et al. | 604/335 |
| 2003/0028160 A1* | 2/2003 | Leise et al. | 604/334 |
| 2003/0167042 A1* | 9/2003 | Poulsen | 604/327 |
| 2004/0049837 A1* | 3/2004 | Falconer et al. | 4/144.1 |
| 2005/0131360 A1 | 6/2005 | Winther | |
| 2006/0111682 A1* | 5/2006 | Schena et al. | 604/334 |
| 2008/0051743 A1 | 2/2008 | Falconer et al. | |
| 2011/0028923 A1 | 2/2011 | Murray | |

* cited by examiner

DRAINABLE OSTOMY POUCH WITH CONCEALED DRAIN CHUTE

FIELD OF THE INVENTION

The present invention relates to the field of ostomy pouches, in particular, drainable ostomy pouches

BACKGROUND TO THE INVENTION

A number of patents and published applications teach a drainable ostomy pouch, the walls of which define a narrowed drain chute for draining the pouch contents. The pouch includes an integrated closure system for sealing the pouch closed by rolling or folding the drain chute towards the main body of the pouch. The closure system includes one or more flaps that fold partly around, under or over, the rolled-up drain chute when in its closed configuration, either as a primary or secondary arrangement for retaining the drain chute in the closed configuration. Examples of patents and published applications of interest in this area include U.S. Published Application No. 2005/0131360 and U.S. Pat. Nos. 3,825,005, 4,519,797, 7,306,581, 6,589,221 and 6,780,172.

For some wearers it would be desirable to conceal more completely and discretely the drain chute when in its closed configuration. The present invention has been devised bearing these issues in mind.

SUMMARY OF THE INVENTION

The invention provides a drainable pouch with first and second flaps on opposite faces of the pouch and extending in the region of the drain chute portion.

In one form, the flaps are each dimensioned such that: (i) when the drain chute portion is in its open condition, the drain chute portion extends beyond a distal end of each flap in a direction away from the collection portion; and (ii) when the drain chute portion is in its closed condition, at least one of the flaps extends beyond the drain chute portion in the direction away from the collection portion. The pouch may further comprise at least one fastener for releasably fastening the flaps closed.

Additionally or alternatively, the flaps each have a periphery that includes a convex curved portion. The pouch may further comprise at least one fastener for releasably fastening the flaps to each other when the drain chute portion is in its closed configuration. The convex curved portions of the flaps may provide the pouch with a convex curved peripheral shape in the region of the drain chute portion.

In another aspect, the invention provides a pouch including a flap disposed on a first face of the pouch, the flap comprising a proximal end, side edges, and a distal end; the flap being dimensioned such that (i) when the drain chute portion is in its closed configuration, at least a portion of the flap is foldable under the drain chute portion to a second face of the pouch opposite the first face, and (ii) the side edges of the flap have a shape that matches the side edges of the pouch in the region of the flap when the flap is folded under the drain chute portion.

In another aspect, the invention provides a pouch including a distributed peelable mechanical engagement fastener part mounted on a wall that is welded within a peripheral seam of the pouch, the distributed mechanical engagement fastener being coextensive with first and second edges of the wall which edges form part of, or extend to, opposite peripheral edge portions of the pouch, and the fastener part extending as a continuous piece between the first and second edges. Such a configuration can facilitate production by stamping or cutting from continuous roll stock. For example, the fastener part may be pre-mounted as a continuous strip on roll stock for forming the wall welded within the pouch seam. This can avoid having to attach a discrete fastener part to a wall of the pouch as a separate operation after the pouch profile has first been formed.

In another alternative, the invention provides a drainable ostomy pouch that comprises: a collection portion; and a drain chute portion depending from the collection portion and having a discharge opening for permitting emptying of contents from the pouch, the drain chute portion being foldable between an open condition in which the drain chute portion is extended from the collection portion, and a closed condition in which the drain chute portion is folded towards the collection portion. The pouch further includes at least one flap that has a profile that integrates with the peripheral shape of the pouch. In one form, two flaps provide a curved convex peripheral profile of the pouch when the drain chute portion is closed. In another alternative, a single flap has flared side edges shaped to match the tapered pouch periphery when the flap is folded under the closed drain chute portion.

Features and advantages achievable by the invention include one or more of: (i) the ability to conceal more discretely the drain chute portion of a drainable pouch; and/or (ii) the ability to provide a drainable pouch with a shape in a lower region that matches a convex rounded shape of a non-drainable pouch.

Additional aspects, features and advantages of the invention will become apparent from the following description of preferred embodiments. Protection may be claimed for any novel feature or idea disclosed herein and/or illustrated in the drawings whether or not emphasis has been placed thereon.

DETAILED DESCRIPTION OF PREFERRED EMBODIMENTS

Preferred embodiments of the invention are now described with reference to the accompanying drawings. The drawings depict ostomy pouches in a generally upright orientation in which the pouches are normally worn. The same reference numerals depict equivalent features in each embodiment.

FIGS. 1 to 5 illustrate a first embodiment of ostomy pouch 10 comprising a front wall 12 and a rear wall 14 of flexible impermeable plastics film, welded together around a common peripheral seam 16. Many suitable materials for the walls 12, 14 are known in the art. For example, the material may be a laminate of one or more layers of ethylene vinyl acetate (EVA) and a barrier layer, for example, of poly vinylidene chloride (PVDC).

The rear wall 14 of the pouch 10 has an entrance aperture 18 in its upper region for receiving human waste from a wearer's stoma. In the illustrated embodiment, the pouch 10 is intended as an ileostomy pouch for receiving semi-solid ileal fluid from a wearer's ileal stoma. The pouch 10 is securable to the peristomal area of the wearer's body by a body fitment, indicated generally at 20. The body fitment 20 typically includes a pad or wafer of hypoallergenic skin adhesive (not shown). The pouch 10 may be of a so-called "one piece" type in which the body fitment 20 is permanently secured to the rear wall 14 of the pouch 10 at or around the entrance aperture 18. Alternatively, the pouch 10 may be of a so-called "two-piece" type in which the pouch 10 and the body fitment 20 are separate items, and are removably attachable to each other by an ostomy coupling. An example coupling includes an adhesive ostomy coupling or a mechanical ostomy coupling.

As is conventional, the pouch 10 may include one or more internal compartments (not shown) for accommodating the human waste collected in the pouch 10. Additionally or alternatively, the pouch 10 may include a known deodorizing filter (not shown) for venting and deodorizing flatus from the interior of the pouch 10. The deodorizing filter may be mounted to communicate with a vent aperture, for example, in one of the front and rear walls 12, 14.

The pouch 10 includes an outlet 22 in the form of a drain chute portion 24 of the pouch 10. The drain chute portion 24 is narrower than the upper portion of the pouch 10. As can be seen in the drawings, the drain chute portion 24 may be disposed generally symmetrically with respect to the entrance aperture 18. However, alternatively (not shown), the drain chute portion 24 may be generally asymmetrical with respect to the entrance aperture 18.

The drain chute portion 24 is defined by extensions of the front and rear walls 12, 14 that are welded together at the sides of the drain chute portion 24. A discharge opening 26 is defined between unsecured distal edges of the front and rear walls 12, 14. In the illustrated embodiment, the front and rear walls 12, 14 are generally coterminous. However, alternatively (not shown), one of the front and rear walls 12, 14 may project beyond the peripheral edge of the other, such that the discharge opening 26 is defined by, or between, stepped walls. Alternatively (not shown), the discharge opening 26 may instead be provided as a slit in one of the walls 12, 14.

There now follows a description of a closure system, integral with the pouch 10, for sealing the drain chute portion 24 closed. While this closure system is highly preferred, other types of integral and non-integral closure systems may be used as desired. An integral closure system is preferred as this can provide a compact size, beneficial to discrete concealment behind one or more flaps used in this invention (as described later). The closure system comprises one or both of:

(a) At least one resiliently flexible reinforcing member 32 attached to at least one of the front and rear walls 12, 14 at the drain chute portion 24. In the illustrated form, the reinforcing member 32 is positioned at, or near, the discharge opening 26. In an alternative form described later with respect to FIGS. 10 and 11, the reinforcing member 32 is spaced from the discharge opening 26. The (or each) reinforcing member 32 may be attached along its length to the wall 12, 14. In the illustrated form, the reinforcing member 32 is attached to the exterior face of the wall 12, 14, but the reinforcing member 32 could instead be attached to the interior face, or embedded in the wall 12, 14. Purposes and advantages of the reinforcing member(s) 32 may include one or more of the following:

(i) to define a unit fold-interval by which the drain chute portion 24 is folded-up into its closed configuration (as described later);

(ii) to enable the degree of distension of the discharge opening 26 to be controlled. For example, the reinforcing member 32 may bias the discharge opening 26 naturally towards an at least partly closed, or constricted condition. The reinforcing member 32 may have a generally planar shape that biases the discharge opening 26 closed, or it may have a curved or bowed natural shape to bias the discharge opening 26 slightly, or fully open, depending on the degree of bowing. The reinforcing member 32 may be manipulated manually, either by squeezing the reinforcing member 32 at its opposite edges to bow the reinforcing member 32, or by pressing the face of the reinforcing member 32 to flatten it. Typically, the reinforcing member 32 is made of a resiliently flexible plastics material that is not compressible. However, a compressible material, such as a compressible foam, may be used if desired; and/or (iii) to provide a seal when the outlet 22 is rolled or folded-up. It is preferred that the reinforcing member 32 extend entirely across the width of the internal passage within the drain chute portion 24, to at least partly overlap the peripheral weld seam 16. If multiple reinforcing members 32 are used, then either at least one reinforcing member 32 extends entirely across the width of the internal passage, or the combined footprint of the reinforcing members 32 extends across the width of the internal passage.

In the illustrated embodiment, two reinforcing members 32 are provided; one attached to each wall 12, 14. The reinforcing members 32 preferably at least partly overlap each other, although the reinforcing members 32 may be partly or wholly offset with respect to each other in an axial and/or transverse direction of the drain chute portion 24 as desired. The reinforcing members 32 are spaced from each other by the film material of one or both walls 12, 14, such that the reinforcing members 32 do not directly contact each other. However, if desired, the reinforcing members 32 may contact each other at one or more points, either permanently, or when the drain chute portion 24 is placed in its closed configuration.

Figure 4:
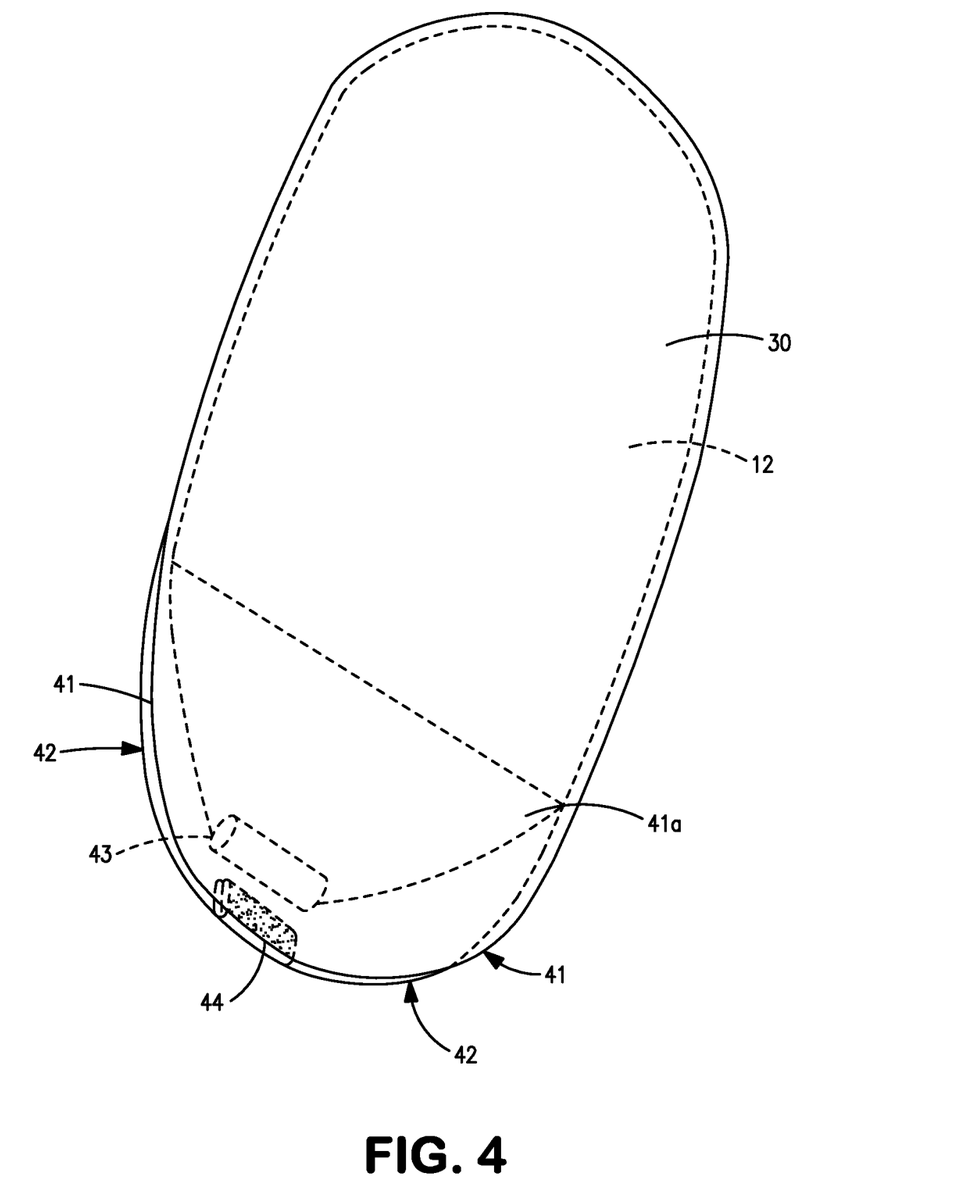
FIG. 4 is a schematic front perspective view similar to FIG. 1, but showing the pouch in its closed configuration.

(b) A fastener for fastening the drain chute portion 24 in a rolled-up closed configuration, as illustrated in FIG. 4. The fastener generally comprises first and second fastener parts 36, 38 on the front and rear walls 12, 14, respectively. Each fastener part 36, 38 may be an element that is attached to the wall 12, 14, or it may comprise a surface of the respective wall 12, 14 itself. In the preferred form, the fastener is a peelable, distributed mechanical engagement fastener, such as a hook-loop type, or an interlocking male-male type, e.g., interlocking mushroom heads, or interlocking hooks. Alternatively, the fastener may be of a peelable-resealable adhesive type, including at least one adhesive surface for adhesively engaging either a complementary adhesive, or non-adhesive, landing surface, such as a wall of the drain chute portion 24. The fastener may be one part. The fastener parts 36, 38 may be the same as each other (in terms of material and/or configuration), or the fastener parts 36, 38 may be different.

In the illustrated embodiment, the reinforcing members 32 and the fastener parts 36, 38 are distinct items from one another. However, at least one of the fastener parts 36, 38 may be integrated with a respective reinforcing member 32, if desired.

Figure 1:
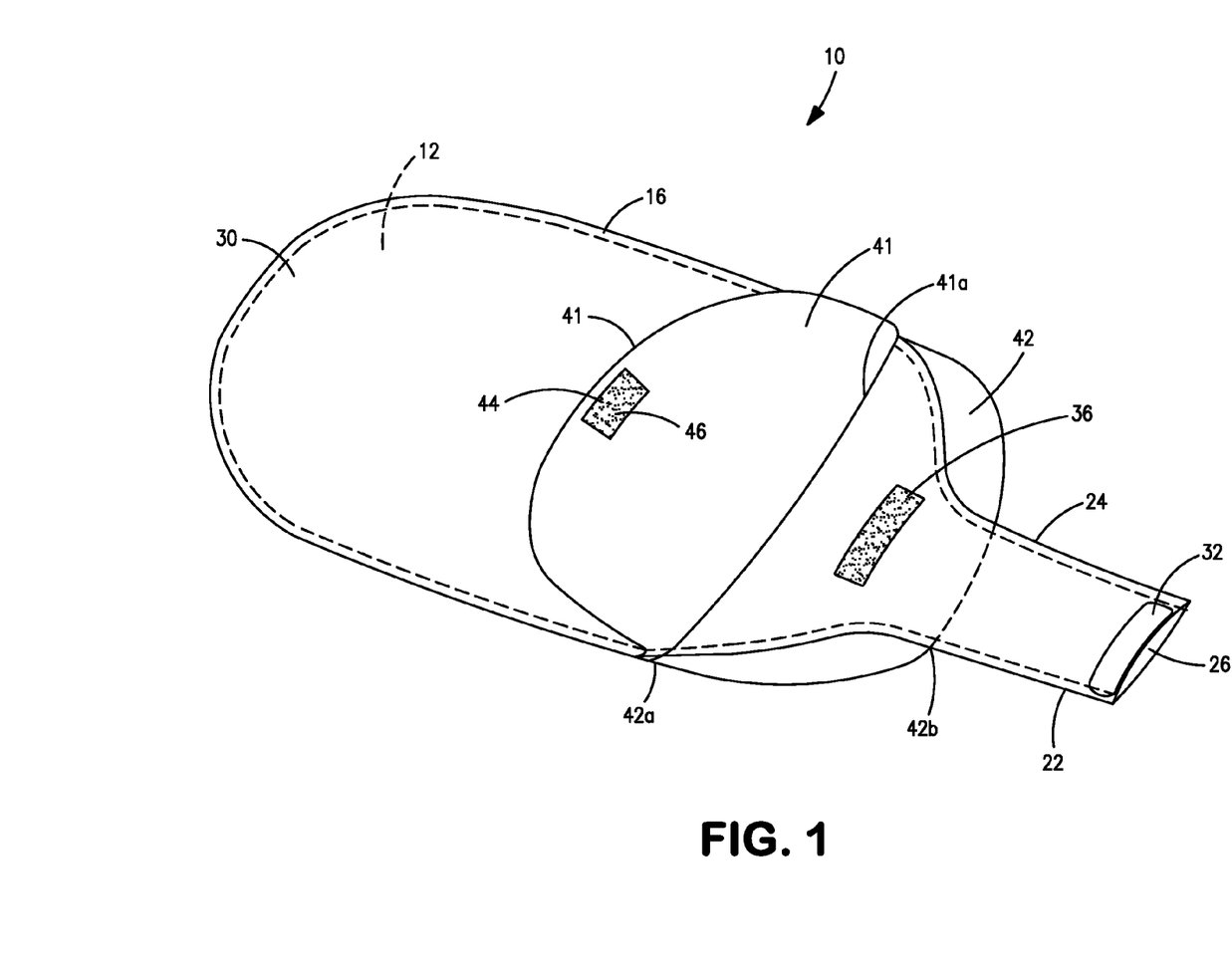
FIG. 1 is a schematic front perspective view of a first embodiment of ostomy pouch in its open configuration.
Figure 2:
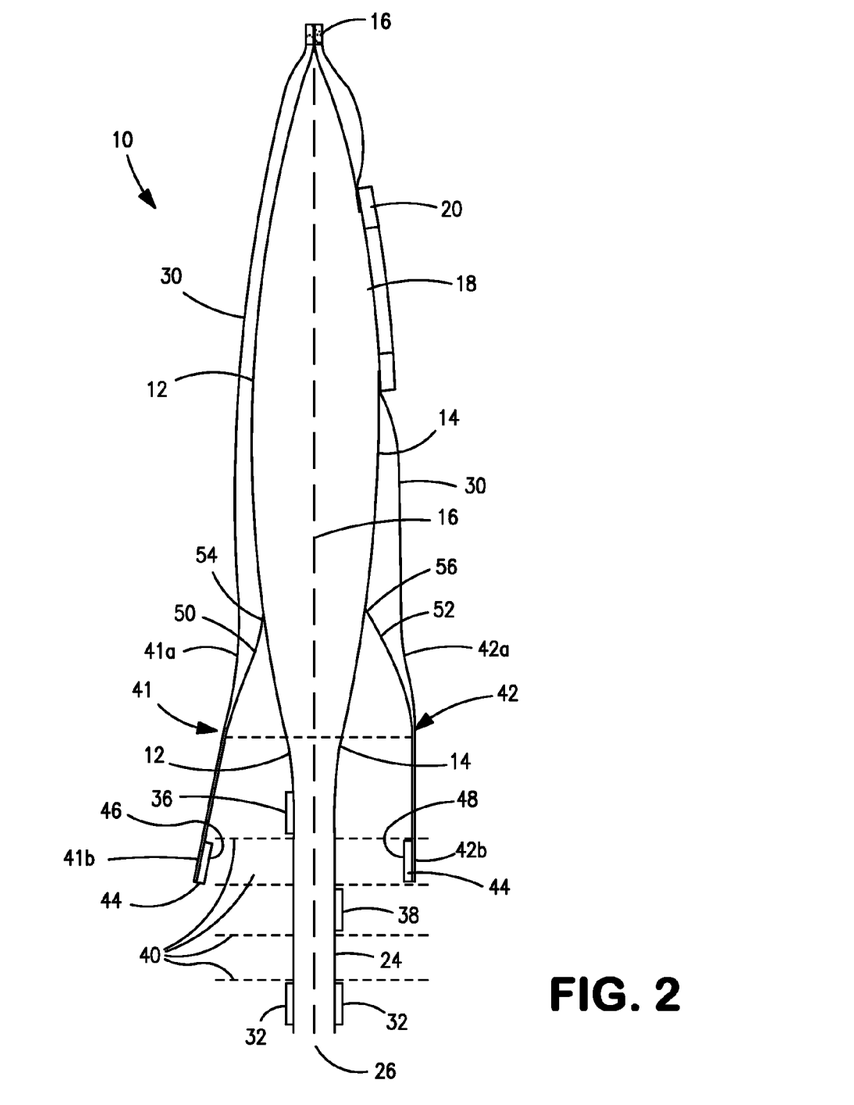
FIG. 2 is a schematic side sectional view through the pouch of FIG. 1.
Figure 2A:
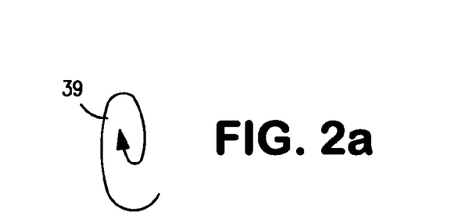
FIG. 2a is a schematic side sectional view showing the folding of the drain chute portion of the pouch of FIG. 1.

FIGS. 1 and 2 show the drain chute portion 24 in its open configuration for permitting discharge of stomal effluent from the pouch 10, in which the drain chute portion 24 extends in a first direction away from the collection portion of the pouch 10. In order to close the drain chute portion 24, the drain chute portion 24 is folded (indicated by arrow 39 in FIG. 2a) one or more times around notional fold lines 40 (such as defined by the unit size of the reinforcing members 32). In this embodiment, the drain chute portion 24 is folded upwardly four times to its closed configuration, but a greater or smaller number of folds may be implemented as desired (e.g., three times in the second embodiment described later). The folding brings the drain chute portion 24 to its closed configuration in which, in this embodiment, a coil 43 is formed. The fastener parts 36, 38 are so positioned that folding of the drain chute portion 24 to its closed position brings the fastener parts 36, 38 into register with each other. The fastener parts 36, 38 are mutually engaged by a finger-pressure squeezing of two fastener parts 36, 38, thereby securing the drain chute portion 24 in its closed position.

As mentioned above, other types of integral or non-integral closure systems may be implemented as desired. For example, either the reinforcing members 32 or the fastener or the fastener parts 36, 38 may be omitted, or an entirely different closure system may be used.

A feature of the present embodiments is the provision of one or more flaps for substantially concealing, discretely, the rolled-up drain chute coil 43. The present embodiment comprises a front flap 41 and a rear flap 42. The flaps 41, 42 may define a pocket that is at least partly closable. Each flap 41, 42 is provided on, or adjacent to, the front or rear wall 12, 14, respectively, to depend in the same direction as the drain chute portion 24 when extended. Each flap 41, 42 includes a proximal portion or end 41a, 42a respectively, and a distal portion or end 41b, 42b, respectively. As can be seen in FIGS. 1 and 2, each flap 41, 42 is dimensioned such that the depending length of the flap 41, 42 is shorter than the length of the drain chute portion 24 when the drain chute portion 24 is in its extended condition. Or, in other words, the drain chute portion 24 extends beyond the distal end 41b, 42b of each flap 41, 42, in a (first) direction away from the collection portion of the pouch 10. The discharge opening 26 is positioned to be clear of the flaps 41, 42. This geometry ensures that, during emptying of the pouch 10 via the discharge opening 26, there is little risk of the effluent contacting and soiling the flaps 41, 42.

Figure 3:
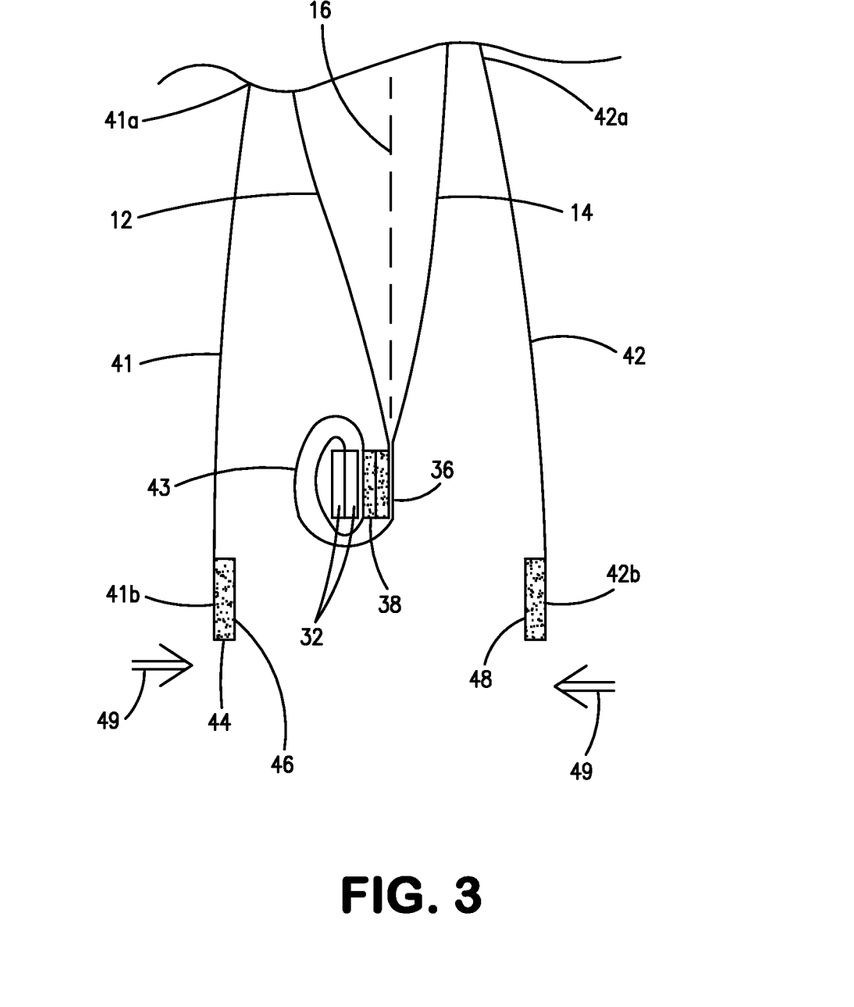
FIG. 3 is a schematic side sectional view through a portion of the first embodiment, with the drain chute portion folded to a closed condition.
Figure 5:
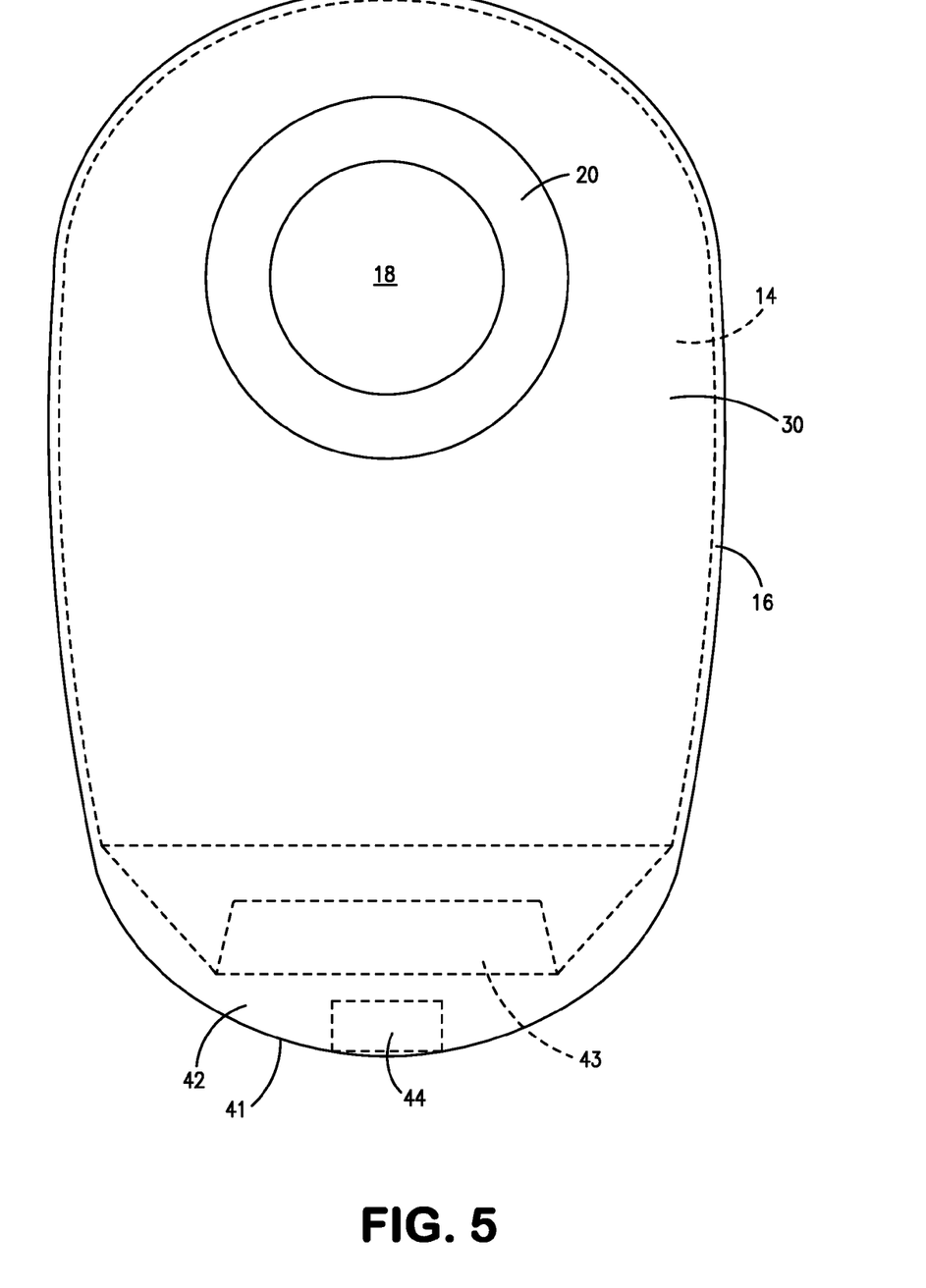
FIG. 5 is a schematic rear view of the pouch in the closed configuration.
Figure 6:
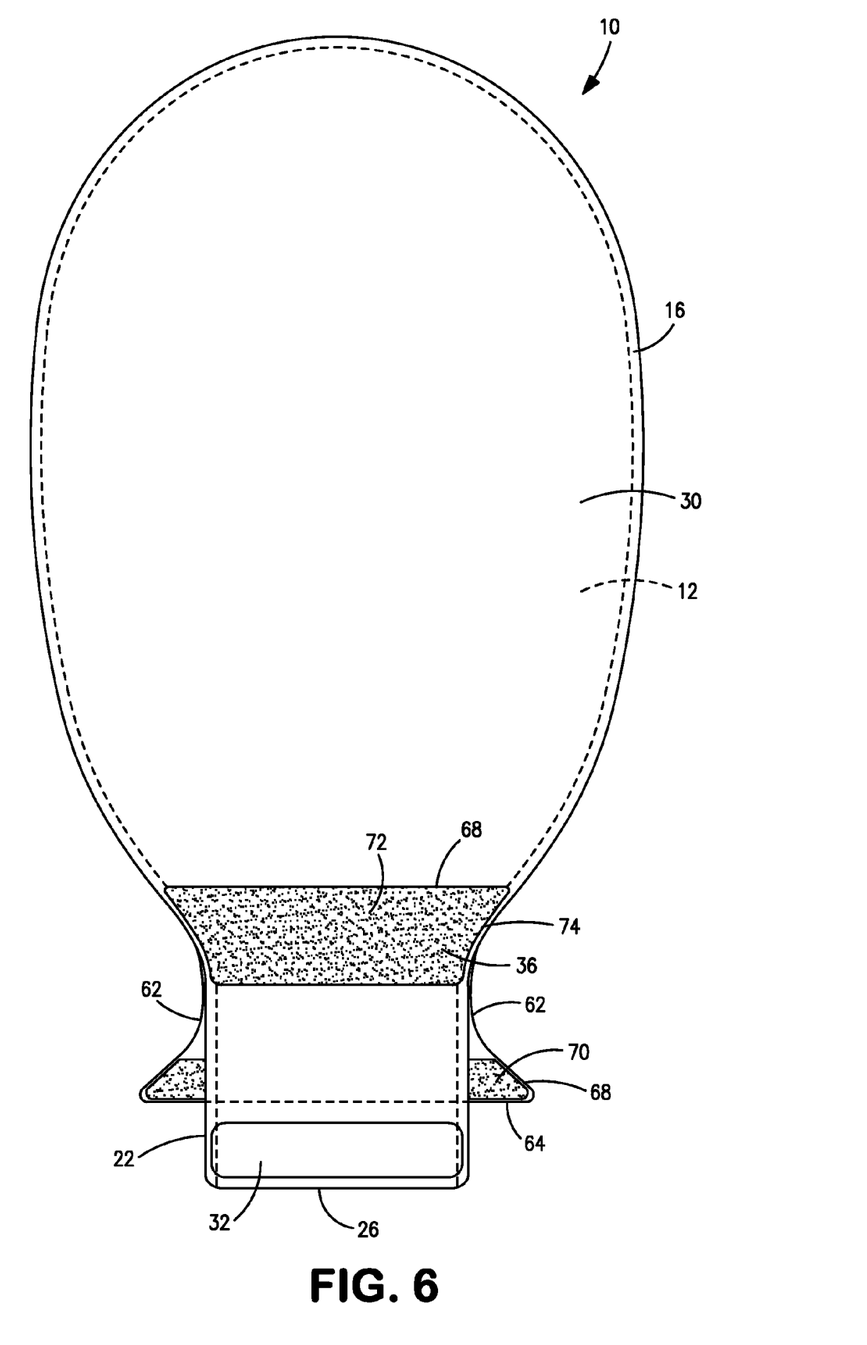
FIG. 6 is a schematic front view of a second embodiment of ostomy pouch in its open configuration.
Figure 7:
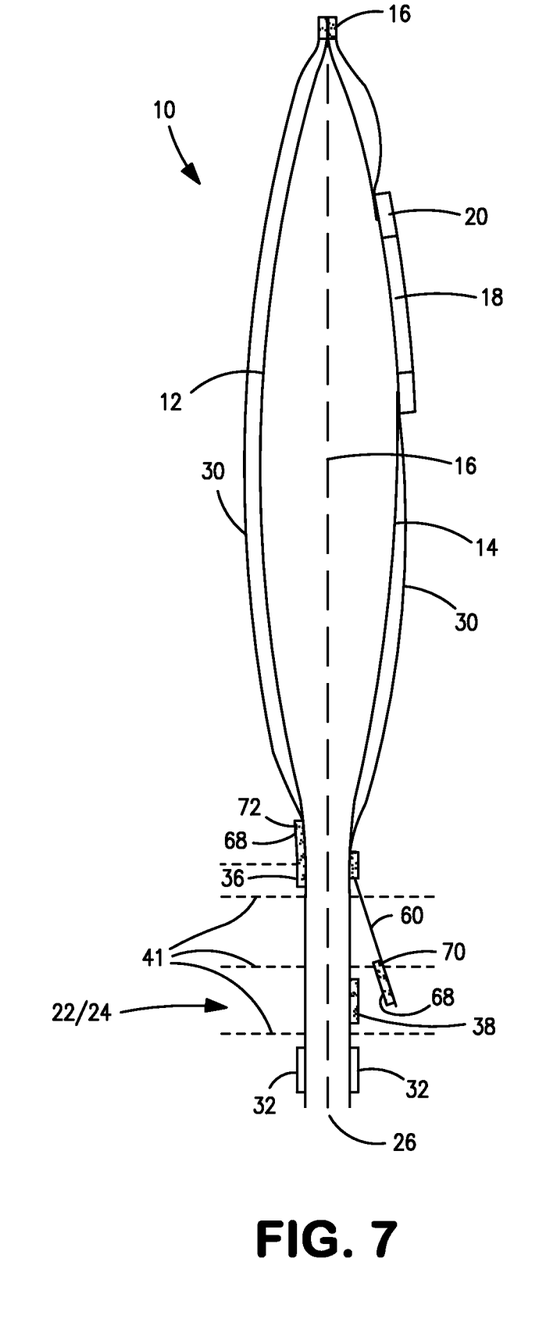
FIG. 7 is a schematic side sectional view through the pouch of FIG. 6.

As can be seen in FIGS. 3-5, the flaps 41, 42 are also dimensioned such that, when the drain chute portion 24 is in its closed coiled configuration, the depending length of at least one of the flaps 41, 42 is longer than the dimension of the coil 43. In other words, the distal end 41b, 42b, of at least one flap 41, 42 projects beyond the periphery of the coil 43 in the (first) direction away from the collection portion of the pouch 10 (and, for example, in all directions). In the illustrated form, both flaps 41, 42 have this feature. Also, optionally, the flaps 41, 42 are substantially the same size and shape, to mirror each other. The flaps 41, 42 are substantially co-terminous with each other.

A flap fastener 44 is provided for releasably fastening the flaps 41, 42 together. The flap fastener 44 may any of the types of fastener described above. Optionally, the flap fastener 44 may be the same type chosen for the fastener. The flap fastener 44 includes complementary surfaces or parts 46, 48. In the illustrated form, the flap fastener parts 46, 48 are positioned such that they do not substantially overlap with the drain chute coil 43. This geometry avoids the flap fastener 44 from increasing the bulk and rigidity of the pouch 10 at the drain chute coil 43. It will be appreciated that the coil 43 itself, including the reinforcing members 32 and/or the fastener may already be less flexible than the remainder of the pouch 10. Avoiding additional rigidity improves comfort for the wearer. The flap fastener 44 also obstructs accidental movement of the drain chute portion 24 to its extended position, when the flap fastener 44 fastens the flaps 41, 42 together. The flap fastener 44 is fastened by pressing the flaps 41, 42 together, as illustrated by arrows 49, once the drain chute portion 24 has been folded to its closed condition.

In the illustrated form, each of the flaps 41, 42 has a generally convex curved outer profile that smoothly continues the general outer shape of the pouch 10 without abrupt changes shape or curvature. This geometry can provide a near perfect impression that the pouch 10 is a closed pouch, and can conceal the drain chute coil 43 effectively and discretely. This is aided by the use of the integral closure system of the preferred embodiment that has a generally low profile without the additional bulk of an external closure clamp.

A further geometric feature is that the flaps 41, 42 attach to each other without substantial folding of either flap 41, 42 under the lower extremity of the pouch 10. This preserves the curved profile of the pouch 10 at its lower end compared to a prior art flap that folds under the lower extremity of the pouch 10. A folding flap 41, 42 would generally be folded along a straight line, resulting in a straight edged profile at the bottom of the pouch 10. Instead, the present embodiment achieves the technically difficult feature of a drainable pouch with a convex rounded profile at its lower extremity, that can more closely resemble a permanently closed pouch.

An exterior face of one or both of the front and rear walls 12, 14 may be at least partly covered by a comfort layer 30. The comfort layer 30 may be an additional panel outside the front wall 12 and/or rear wall 14, and secured to the pouch 10 at, for example the peripheral seam 16. Alternatively, the comfort layer 30 may be a surface layer carried by, or forming part of, the respective wall 12, 14. The comfort layer 30 is typically made of a soft cushioning material. A typical material includes a woven, nonwoven, or an apertured plastics film. The comfort layer 30 may be elastically stretchable, or it may be substantially non-stretchable. The comfort layer 30 is typically made of a soft cushioning material. The flaps 41, 42 may each be made of, or comprise, a comfort layer 30. In the preferred form, the comfort layer 30 on the flaps 41, 42 is an extension of the comfort layer 30 on the respective pouch wall 12, 14. Such an arrangement enhances the visual effect of a closed pouch, with a substantially smooth and uninterrupted face or surface region, especially near the lower extremity of the pouch 10.

Each flap 41, 42 may further comprise a backing layer 50, 52, respectively. The backing layers 50, 52 may, for example, made of the same film material as the pouch walls 12, 14. Alternatively, the backing layers 50, 52 may be an extension of the comfort layer 30 that is folded back on itself, such that each flap 41, 42 consists of plural layers or plies of comfort layer material. The backing layers 50, 52 may extend to the pouch walls 12, 14 and attached at points 54, 56, respectively.

In the illustrated form, the flaps 41, 42, and the flap fastener 44 provide a secondary retainer for retaining the drain chute portion 24 in its closed coiled configuration. Alternatively, the closure fastener may be omitted, and the flaps 41, 42 and flap fastener 44 may provide a primary retainer for retaining the drain chute portion 24 in its closed configuration.

In the first embodiment, neither flap 41, 42 is folded underneath the folded-up drain chute coil 43. However, such a folding flap may be used, as shown in the second embodiment. Referring to FIGS. 6-9, the second embodiment of ostomy pouch 10 is similar to the first embodiment in terms of the pouch construction, the drain chute portion 24, and the closure system for the drain chute portion 24. The main difference lies in the provision of a profiled flap 60 on one side of the pouch 10, instead of a pair of flaps 41, 42 of the previous embodiment.

Figure 8:
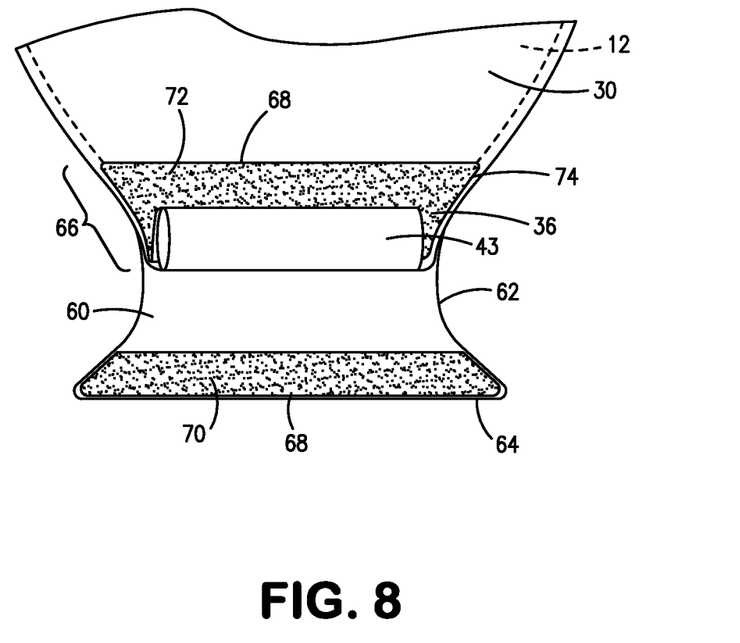
FIG. 8 is a schematic front view of the second embodiment of pouch with the drain chute in its closed configuration
Figure 9:
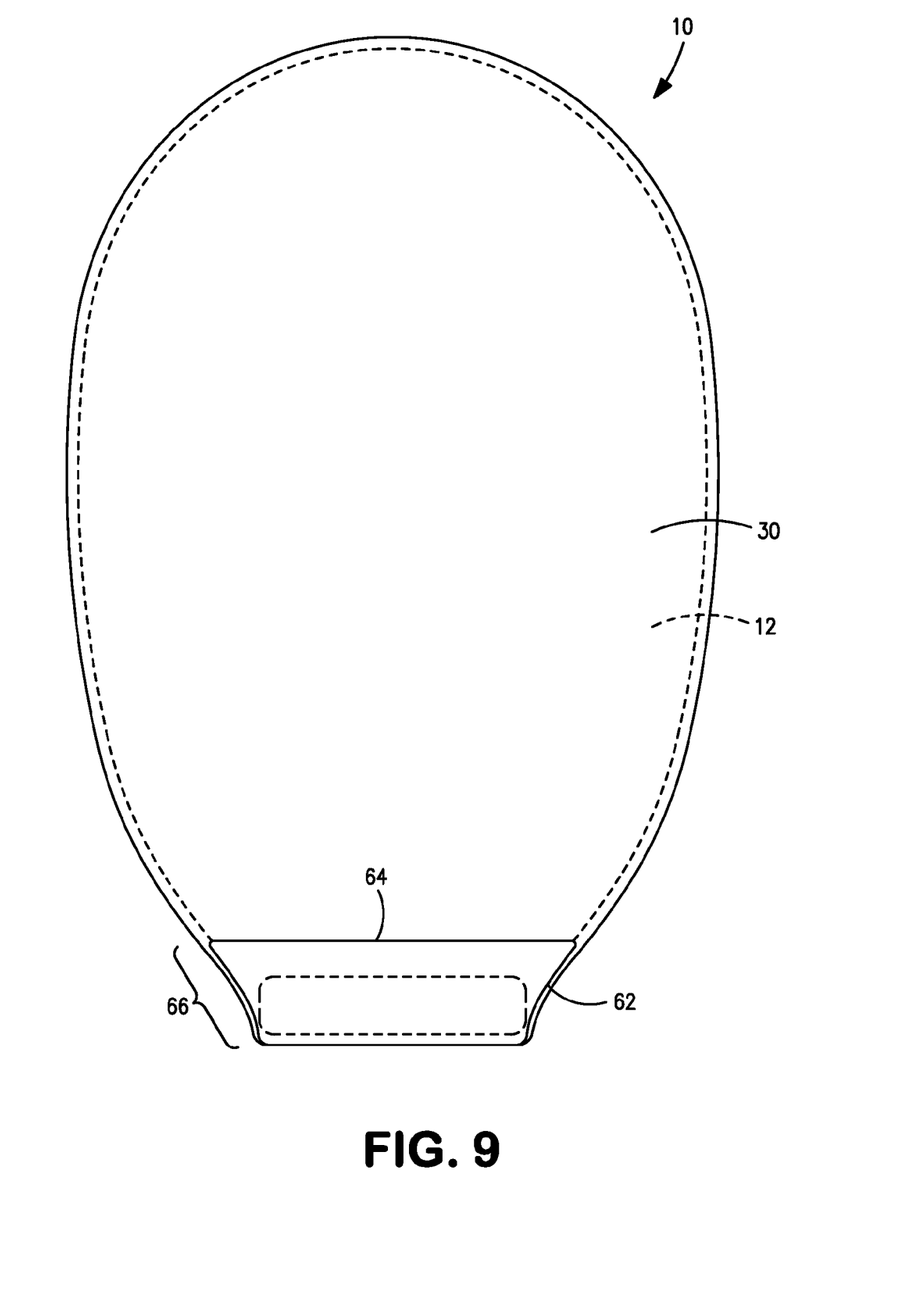
FIG. 9 is a schematic front view similar to FIG. 8, showing the flap in its closed position.

The profiled flap 60 has side edges 62 that flare outwardly towards a distal region or end 64 of the profiled flap 60. The profiled flap 60 is dimensioned such that, when the drain chute portion 24 is in its extended condition (FIGS. 6 and 7), the depending length of the profiled flap 60 is shorter than the length of the drain chute portion 24. Or, in other words, the drain chute portion 24 extends beyond the distal end 64 of the profiled flap 60. The discharge opening 26 is positioned to be clear of the profiled flap 60. This geometry ensures that, during emptying of the pouch 10 via the discharge opening 26, there is little risk of the effluent contacting and soiling the profiled flap 60. As can be seen in FIG. 8, the profiled flap 60 is also dimensioned such that, when the drain chute portion 24 is in its closed coiled configuration, the depending length of the profiled flap 60 is longer than the dimension of the coil 43. In other words, the distal end 64 projects beyond the periphery of the coil 43 allowing the profiled flap 60 to be folded under the coil 43 to the other face of the pouch 10 (FIG. 9). The side edges 62 are shaped such that, when the profiled flap 60 is folded around (under) the folded-up drain chute coil 43 as in FIG. 9, the side edges 62 follow generally the same profile shape as the portion 66 of the periphery of the pouch 10 that confronts the profiled flap 60. The side edges 62 may be generally in register or coextensive with the portion 66 of the periphery, or side edges 62 and the portion 66 of the pouch periphery may be disposed one slightly inboard of the other. The degree of offset may be less than 5 mm, preferably less than 4 mm, more preferably less than 3 mm, and most preferably less than 2 mm. The portion 66 may be taper towards the drain chute portion 24, in a trapezoid form (either with straight or curved tapered sides). The side edges 62 may define a similar trapezoid shape, such that the profiled flap 60 appears to have triangular wings at its sides compared to the drain chute portion 24.

A flap fastener 68 is provided for retaining the flap 60 when in its folded configuration. The flap fastener 68 comprises a first fastener surface or part 70 at or near the distal end 64 of the profiled flap 60, and a second fastener surface or part 72 on the opposite side of the pouch 10 to the profiled flap 60. The flap fastener 68 may any of the types of fastener described above. Optionally, the flap fastener 68 may be the same type chosen for the fastener. The first flap fastener part 70 on the profiled flap 60 generally extends across the entire width of the distal end 64 of the profiled flap 60, and is dimensioned to match substantially the size of the second flap fastener part 72.

An advantage of the profiled flap 60 matching the profile of the pouch 10 when the profiled flap 60 is folded under or around the drain chute coil 43 is that it facilitates the production of the pouch 10 using of material in continuous roll stock form, to which the respective fastener part 70, 72 has been pre-attached, also in continuous form. For example, the pre-attached second fastener part 72 on the face of the pouch 10 is cut or stamped from the roll stock during manufacture in the shape of the pouch outline, such that the pre-attached second fastener part 72 is cut or stamped with a shape matching the pouch profile. The second fastener part 72 extends substantially as a continuous piece from one cut or stamped peripheral edge of the pouch 10 to the opposite edge. This avoids the need to have to attach a discrete second fastener part 72 to the pouch face as a separate operation, thereby simplifying the manufacturing process and reducing cost. Similarly, the profiled flap 60 is, for example, cut or stamped from roll-stock material to which the first fastener part 70 is pre-attached as a continuous strip. The profiled flap 60 and the first fastener part 70 are shaped together by the single cutting or stamping operation. The first fastener part 70 extends substantially as a continuous piece from one cut or stamped peripheral edge of the profiled flap 60 to the opposite edge; these edges extend to the welded periphery of the collection portion of the pouch 10. This also avoids having to attach a discrete fastener part to the profiled flap 60, providing the same manufacturing improvements and efficiencies as mentioned for the second fastener part 72.

In use, the matching shapes of the profiled flap 60 and the portion 66 of the pouch periphery ensure that the profiled flap 60 (and the respective first fastener part 70) substantially cover the second fastener part 72 on the face of the pouch 10. This substantially avoids exposed fastener surface of the second fastener part 72 that could otherwise catch on the wearer's clothing or undergarments, or irritate the skin.

In the illustrated form, the fastener parts 70, 72 are portions of the same fastener part or member 74. The second flap fastener part 72 engaged by the first fastener part 70 on the profiled flap 60 is an upper portion of the fastener member 74, and the first fastener part 70 is a lower portion of the fastener member 74. The fastener member 74 has a shape that generally matches the shape of the portion 66 of the pouch periphery in the region of the fastener member 74. The fastener member 74 may be coextensive with the portion 66 of the pouch periphery, or it may be slightly inboard of the portion 66 of the pouch periphery to provide a zone of pouch wall material as a comfort cushion with respect to the edge of the fastener member 74.

Using a coextensive fastener member 74 can enable the fastener member 74 to be pre-attached to roll-stock material, as a continuous strip in the same manner as described above. The first flap fastener part 70 on the profiled flap 60 generally extends across the entire width of the upper portion second fastener part 72 of the fastener member 74, and the profiled flap 60 covers any exposed portion of the fastener member 74 not engaged by the first fastener part 70 or fastener part 38.

As in the first embodiment, the pouch 10 may carry a comfort layer 30 on the front wall 12 and/or the rear wall 14. The comfort layer 30 may extend to cover a face of the profiled flap 60. In one form, the profiled flap 60 substantially consists of one or more plies of comfort layer material. In another alternative (not shown), the flap 60 further comprises a backing film, in a similar manner to the first embodiment. The fastener parts 70, 72 and/or the fastener member 74 may be mounted on the comfort layer 30. In a preferred form, the fastener parts are pre-mounted as continuous pieces on respective portions of comfort layer material in roll stock form. The shapes of the fastener parts 70, 72 are defined when the comfort layer material is cut or stamped from the roll stock and welded in the peripheral seam 16.

In use, the drain chute portion 24 is folded to its closed coiled configuration, and the profiled flap 60 is folded under the coil 43 and fastened by the fastener 68. The profiled flap 60 substantially covers and conceals the drain chute coil 43, and is discretely arranged by virtue of the profiled flap 60 matching the profile of the pouch periphery. The profiled flap 60 can be considerably more discrete than, for example, a straight edged rectangular shaped flap that has a shape different from the pouch periphery.

In the illustrated form, the profiled flap 60 depends from the rear wall 14 of the pouch 10, and is folded under the coil 43 to the front wall 12. However, it will be appreciated that the arrangement of the profiled flap 60 could be reversed, if desired, so that the profiled flap 60 would depend from the front wall 12. The folding direction of the drain chute portion 24 could also be reversed, if desired, although it will be appreciated that the folding direction of the drain chute portion 24 can be independent of whether the profiled flap 60 is disposed on the front or rear wall 12, 14 of the pouch 10.

In the illustrated form, the profiled flap 60 and the flap fastener 68 provide a secondary retainer for retaining the drain chute portion 24 in its closed coiled configuration. In a modified form, the closure fastener may be omitted, and the profiled flap 60 and flap fastener 68 may provide a primary retainer for retaining the drain chute portion 24 in its closed configuration.

Although the feature of a fastener part 70, 72 being coextensive with the wall 12, 14 on which the fastener part 70, 72 is carried, and enabling that wall to be cut from roll stock on which the fastener part 70, 72 is pre-mounted as a continuous piece, is only described in detail for the second embodiment, it will be appreciated that the first embodiment may also incorporate this idea.

Figure 10:
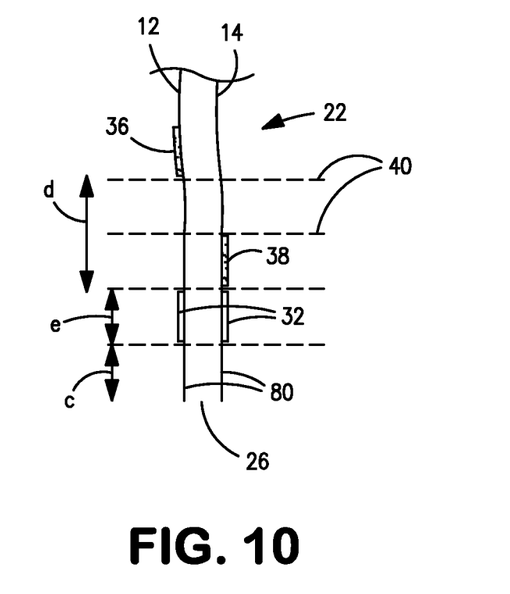
FIG. 10 is a schematic partial sectional view showing a modified drain chute in an open position.
Figure 11:
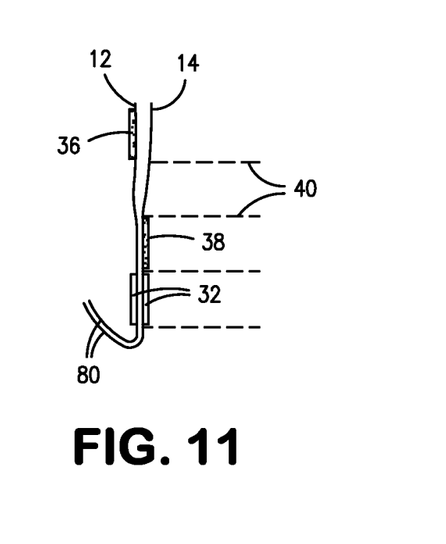
FIG. 11 is a schematic partial sectional view similar to FIG. 10, showing the drain chute portion with an initial fold towards a closed position with the roll started below the reinforcing member.

FIGS. 10 and 11 illustrate a modification to the arrangement of reinforcing members 32 on the drain chute portion 24. This modification may be used with or without the flap arrangements described above. The main difference in the modification is that at least one reinforcing member 32 is spaced from the discharge opening 26 by a distance "c" that is at least 0.5 cm, more preferably at least 1 cm, more preferably at least or about 1.5 cm. Spacing the reinforcing member 32 from the discharge opening 26 can improve hygiene for the wearer by providing a guard distance between the draining effluent, and the point at which the wearer has to handle the pouch 10 at the reinforcing member(s) 32. This can also reduce the risk of the wearer's hands being soiled by splashback from the draining effluent (which may have a highly fluid consistency). The spacing can still permit the wearer to controllably distend the drain chute portion 24 for cleaning after draining.

If an outlet fastener is provided (not shown), the reinforcing member 32 is positioned between a respective outlet fastener part 36, 38, and the discharge opening 26. When rolling up the drain chute portion 24 into a closed position, the wearer can begin the first fold either below reinforcing member 32 (FIG. 11) or above it (not shown). embodiment, the distance "c" is not greater than a distance "d" between the reinforcing member 32, and the respective fastener part 36 that is furthest from the discharge opening 26. Such a distance "c" ensures that a region 80 of the drain chute portion 24 between the reinforcing member 32 and the discharge opening 26 can be folded upwardly to start the folding operation, without obscuring the fastener part 36.

Figure 11A:
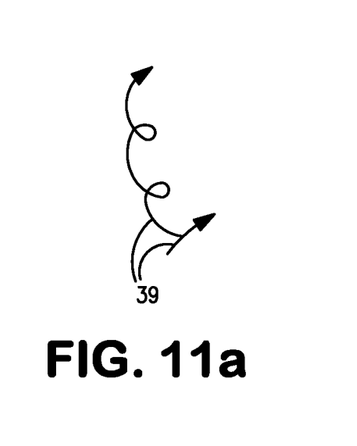
FIG. 11a is a schematic side sectional view showing the folding of the drain chute portion of the pouch of FIG. 11.

In a highly preferred form, the distance "c" is approximately equal to or slightly less than a dimension "e" of the reinforcing member 32 that defines a unit fold length of the drain chute portion 24 (i.e., the distance between the notional fold lines 40). Such a length allows the drain chute portion 24 to be folded either below reinforcing member 32 or above it, without the material below the reinforcing strips 32 interfering with the fastener engagement. The height A of the drain chute portion 24 as rolled preferably does not exceed the height C of the bottom of fastener 36, or most preferably does not exceed height B of the top of the formed coil 43 (not shown). The drain chute portion 24 may be folded as indicated by arrow 39 in FIG. 11a.

In an additional aspect, the invention provides a folding drain chute portion 24 for an ostomy pouch 10, the drain chute portion 24 comprising at least one reinforcing member 32 provided on a face of the drain chute portion 24 and spaced from a discharge opening 26 of the drain chute portion 24 to define a region of plastics pouch film on the face between the reinforcing member 32 and the discharge opening 26. The spacing may be at least 0.5 cm, more preferably at least 1 cm, and more preferably at least or about 1.5 cm. A footprint of the at least one reinforcing member 32 may extend substantially entirely across an internal drain passage in the drain chute portion 24, and preferably overlap weld seams 16 on either side of the internal drain passage. Where the reinforcing member 32 defines a unit fold length of the drain chute portion 24, the spacing may optionally be approximately the same as said unit fold length. As described earlier above, the reinforcing member(s) 32 may be substantially planar to bias the drain chute portion 24 and/or outlet 22 opening closed, or the reinforcing member(s) 32 may be slightly or substantially pre-bowed to bias the outlet 22 opening and/or drain chute portion 24 open.

It is emphasized that the foregoing embodiments are illustrative of preferred forms of the invention. Many modifications, improvements and equivalents may be used within the scope and/or spirit of the invention as claimed.

I claim:

1. A drainable ostomy pouch comprising:
    a collection portion for collecting waste from a stoma, the collection portion comprising opposite faces joined together at a common peripheral seam that defines a general outer shape of the collection portion;
    a drain chute portion depending from the collection portion and having a discharge opening for permitting emptying of contents from the pouch, the drain chute portion being foldable between an open condition in which the drain chute portion is extended in a first direction from the collection portion, and a closed condition in which the drain chute portion is folded towards the collection portion;
    first and second flaps each having a proximal end secured to the opposite faces of the collection portion intermediate its length and extending proximate to the drain chute portion, the flaps each being dimensioned such that: (i) when the drain chute portion is in the open condition, the drain chute portion extends beyond a distal end of each flap in said first direction; and (ii) when the drain chute portion is in the closed condition, at least one of the flaps extends beyond the drain chute portion in said first direction; and at least one fastener for releasably fastening the flaps closed, wherein when the drain chute portion is in the closed condition the pouch has a convex curved peripheral shape in the region of the drain chute portion, and wherein each of the flaps has a generally convex curved outer profile that distally extends from the proximal end to smoothly continue the general outer shape of the collection portion without abrupt changes in shape or curvature.

2. The drainable ostomy pouch of claim 1, wherein both the first and second flaps are dimensioned such that when the drain chute portion is in the closed condition, both of the flaps extend beyond the drain chute portion in said first direction.

3. The drainable ostomy pouch of claim 1, wherein said at least one fastener comprises a fastener for releasably fastening the flaps to each other.

4. The drainable ostomy pouch of claim 3, wherein the flap fastener comprises a respective fastener part or surface provided at the distal end of each flap.

5. The drainable ostomy pouch of claim 1, wherein the fastener is positioned so as to fasten the flaps to each other at a position below the level of the drain chute portion when the drain chute portion is in the closed configuration.

6. The drainable ostomy pouch of claim 1, wherein the first and second flaps are of the same size and shape as each other.

7. The drainable ostomy pouch of claim 1, wherein the first and second flaps are dimensioned such that the flaps are coterminous with each other.

8. The drainable ostomy pouch of claim 1, wherein the first and second flaps each have a convex curved shape.

9. The drainable ostomy pouch of claim 1, wherein at least one of the flaps comprises a comfort layer material.

10. The drainable ostomy pouch of claim 1, further comprising at least one reinforcing member disposed near or at a discharge opening of the drain chute portion, the reinforcing member being stiffer than material of the drain chute portion.

11. The drainable ostomy pouch of claim 1, further comprising at least one fastener for releasably retaining the drain chute portion in the closed condition.

* * * * *